(12) United States Patent
Presura et al.

(10) Patent No.: US 10,376,164 B2
(45) Date of Patent: Aug. 13, 2019

(54) VITAL SIGNS SENSOR AND METHOD OF MEASURING VITAL SIGNS OF A USER

(71) Applicant: KONINKLIJKE PHILIPS N.V., Eindhoven (NL)

(72) Inventors: Cristian Nicolae Presura, Veldhoven (NL); Andrei Nicolae, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/763,474

(22) PCT Filed: Sep. 28, 2016

(86) PCT No.: PCT/EP2016/073030
§ 371 (c)(1),
(2) Date: Mar. 27, 2018

(87) PCT Pub. No.: WO2017/055307
PCT Pub. Date: Apr. 6, 2017

(65) Prior Publication Data
US 2018/0303358 A1 Oct. 25, 2018

(30) Foreign Application Priority Data
Sep. 28, 2015 (EP) .................... 15187156

(51) Int. Cl.
*A61B 5/00* (2006.01)
*A61B 5/024* (2006.01)
(Continued)

(52) U.S. Cl.
CPC ........ *A61B 5/02427* (2013.01); *A61B 5/7214* (2013.01); *A61B 5/0082* (2013.01);
(Continued)

(58) Field of Classification Search
CPC . A61B 5/02427; A61B 5/7214; A61B 5/0295; A61B 5/0261; A61B 5/0082; A61B 5/14551; A61B 2562/0238
See application file for complete search history.

(56) References Cited

U.S. PATENT DOCUMENTS 7,727,159 B2    6/2010    Choi et al.
8,768,424 B2    7/2014    Crowe et al.
(Continued)

FOREIGN PATENT DOCUMENTS

RU    99946 U1    12/2010
WO    9403102 A1    2/1994

OTHER PUBLICATIONS

Lee, et al., "The Periodic Moving Average Filter for Removing Motion Artifacts from PPG Signals", International Journal of Control, Automation, and Systems, vol. 5, No. 6, pp. 701-706, Dec. 2007.

(Continued)

*Primary Examiner* — Eric F Winakur
*Assistant Examiner* — Abid A Mustansir

(57) ABSTRACT

PPG sensor emits light at at least three wavelengths ($Y_1$-$Y_3$) and detects the reflected light. The PPG sensor comprises a motion correction unit (130) for correcting motion artefacts from the detected light signals by subtracting the output signal of the detected light at the second wavelength ($Y_2$) from an average of an output signal of the detected light at the first and third wavelength ($Y_1$, $Y_3$). The three wavelengths ($Y_1$-$Y_3$) are arranged around 550 nm. The second wavelength ($Y_2$) is arranged equal distantly between the first and third wavelength.

20 Claims, 6 Drawing Sheets

(51) Int. Cl.
  *A61B 5/026* (2006.01)
  *A61B 5/0295* (2006.01)
  *A61B 5/1455* (2006.01)

(52) U.S. Cl.
  CPC .......... *A61B 5/0261* (2013.01); *A61B 5/0295* (2013.01); *A61B 5/14551* (2013.01); *A61B 2562/0238* (2013.01)

(56) References Cited

U.S. PATENT DOCUMENTS

| | | |
|---|---|---|
| 2005/0038249 A1 | 2/2005 | Denny et al. |
| 2008/0081972 A1* | 4/2008 | Debreczeny ....... A61B 5/14552 600/323 |
| 2014/0276145 A1 | 9/2014 | Banet et al. |
| 2015/0025393 A1 | 1/2015 | Hong et al. |
| 2015/0190096 A1 | 7/2015 | Zong et al. |

OTHER PUBLICATIONS

Tamura, et al., Wearable Photoplethysmographic Sensors—Past and Present, Electronics 2014, 3, pp. 282-302.

* cited by examiner

US 10,376,164 B2

VITAL SIGNS SENSOR AND METHOD OF MEASURING VITAL SIGNS OF A USER

This application is the U.S. National Phase application under 35 U.S.C. § 371 of International Application No. PCT/EP2016/073030, filed on Sep. 28, 2016, which claims the benefit of European Application No. 15187156.3, filed Sep. 28, 2015. These applications are hereby incorporated by reference herein.

FIELD OF THE INVENTION

The invention relates to a vital signs sensor as well as to a method of measuring vital signs of a user.

BACKGROUND OF THE INVENTION

Optical heart rate sensors are well known to monitor or detect vital signs like a heart rate of a user. Such a heart rate sensor can be based on a photoplethysmographic (PPG) sensor and can be used to acquire a volumetric organ measurement. By means of optical pulse sensors or pulse oximeters, changes in light absorption of a human skin are detected and based on these measurements a heart rate or other vital signs of a user can be determined. The PPG sensors comprise a light source like a light emitting diode (LED) which is emitting light into the skin of a user. The emitted light is scattered in the skin and is at least partially absorbed by the blood. Part of the light exits the skin and can be captured by a photo detector. The amount of light that is captured by the photo detector can be an indication of the blood volume inside the skin of a user. A PPG sensor can thus monitor the perfusion of blood in the dermis and subcutaneous tissue of the skin through an absorption measurement at a specific wave length. If the blood volume is changed due to the pulsating heart, the scattered light coming back from the skin of the user is also changing. Therefore, by monitoring the detected light signal by means of the photo detector, a pulse of a user in his skin and thus the heart rate can be determined. Furthermore, compounds of the blood like oxygenated or de-oxygenated hemoglobin as well as oxygen saturation can be determined, when at least two colors are used.

The pulse signal of a heart beat can be detected by photoplethysmography PPG which is measuring a variation in the blood volume of the human tissue. In a PPG sensor, light emitting diodes e.g. at wavelengths between 520 nm (green) and 850 nm (infrared) are used to emit light onto the skin of a user. Transmission type PPG measurements are performed with light at wavelength ranges of 650-850 nm while reflective type PPG sensing is used at 520-570 nm.

Light is scattered in the skin of the user and some of the light is absorbed by blood. The reflected light exits the skin and can be detected by a photo diode. The output signal of the photo diode can therefore be an indication of the blood volume as well as the variation of the blood volume, i.e. the pulse in the skin of a user.

FIG. 1 shows a graph indicating an output signal of a PPG sensor according to the prior art without a movement. In the graph, the heart rate or pulse signal is clearly detectable.

However, in the presence of movement, the output signal of the PPG sensor can be distorted.

FIG. 2 shows an output signal of a PPG sensor according to the prior art without a motion and in the presence of motion. In FIG. 2, the output voltage V of the PPG sensor is depicted over time. In the region A1 as well as in the region A3, no motion is present. Motion is, however, present in the region A2. As can be seen in the region A2 because of the influence of motion, the pulse signals are harder to be determined. A large part of the artefacts in the region A2 is due to blood in the veins of a user as the blood pressure is smaller in the veins.

U.S. Pat. No. 7,727,159 B2 discloses a PPG sensor with a motion artefact correction capability.

SUMMARY OF THE INVENTION

It is an object of the invention to provide a vital signs sensor with an increased signal to noise ratio by eliminating motion artefacts in the output signal of the vital signs sensor.

According to an aspect of the invention an optical vital signs sensor is provided to measure or determine vital signs of a user. The optical vital signs sensor can be a photoplethysmographic sensor (PPG). A light source is configured to generate at least three wavelengths which are directed towards a skin of the user. The sensor also comprises a photo detector unit configured to detect an intensity of light at the at least three wavelengths, wherein said light is indicative of a reflection of light emitted in or from the skin of the user. The sensor also comprises a motion correction unit configured to correct motion artefacts from the light intensity detected by the photo detector by subtracting the light intensity detected at the second wavelength from an average of the light intensity detected at the first wavelength and that at the third wavelength. The first, second and third wavelengths are arranged approximately around 550 nm. The second wavelength is arranged at an equidistant position or wavelengths between the first and second wavelength. As an example, the first wavelength is 530 nm, the second wavelength is 550 nm and the third wavelength is 570 nm.

According to an aspect of the invention, the second wavelength corresponds to a sum of the first and third wavelength divided by 2. If the first, second and third wavelength is selected accordingly, this results in an easy and effective motion artefact correction.

According to a further aspect of the invention, the second wavelength corresponds to approximately 550 nm. Accordingly, the first wavelength may be 530 nm while the third wavelength is 570 nm. Alternatively, the first wavelength may be 540 nm while the third wavelength can be 560 nm.

According to a further aspect of the invention, a method of measuring or determining vital signs of a user with an optical vital signs sensor configured to measure or determine vital signs of a user is provided. The optical vital signs sensor is a PPG sensor. Light is generated at at least three wavelengths and is directed to what a skin of a user. An intensity of light which is indicative of a reflection of light emitted in or from the skin of a user is detected at the at least three wavelengths. Motion artefacts are corrected from the detected light by subtracting the light intensity detected at the second wavelength from an average of the light intensity detected at the first wavelength, and at the third wavelength, The first, second and third wavelengths are arranged approximately around 550 nm. The second wavelength is arranged equidistantly between the first and third wavelength.

According to a further aspect of the invention, a computer program for monitoring a heart rate of a user in an optical vital signs sensor as defined above is provided. The computer program comprises program code means for causing the optical vital signs sensor to carry out the steps of the method measuring or determining vital signs of a user when the computer program is run on a computer controlling the optical vital signs sensor or when the computer program is run in the optical vital signs sensor.

According to an aspect of the invention, the vital signs sensor comprises a LED based PPG sensor. The LED light penetrates the skin of the user, is reflected and some of it can reach a photo detector. The output of the photo detector can be used to monitor a blood volume fraction and blood compounds like oxygenated and de-oxygenated hemoglobin. In particular, the amount of absorption or reflectance of the light from the LED light source can be used to determine the heart rate as well as the blood volume fraction or blood compounds. The heart rate relates to the blood volume fraction. Furthermore, the PPG sensor according to the invention is therefore an optical sensor allowing a non-invasive measurement of vital signs of a user.

According to an aspect of the invention a PPG sensor is provided for measuring or detecting a heart rate of a user. The PPG sensor comprises at least one light source such as a LED and at least one photo detector such as photo diode. The signal received by the photo diode is processed to determine the heart rate of a user. In order to correct any motion artifacts which were generated by a motion of the user while wearing the PPG sensor, a light at three different wavelengths which are equidistant from each other and which are arranged around 550 nm are emitted by the PPG sensor. In order to remove the motion artifacts from the output signals of the photo detector the output signal of the photo detector and the second wavelength is subtracted from the average output signal of the photo detector at the first and at the third wavelength.

It shall be understood that a preferred embodiment of the present invention can also be a combination of the dependent claims or above embodiments or aspects with respective independent claims.

These and other aspects of the invention will be apparent from and elucidated with reference to the embodiment(s) described hereinafter.

DETAILED DESCRIPTION OF EMBODIMENTS

Figure 1:
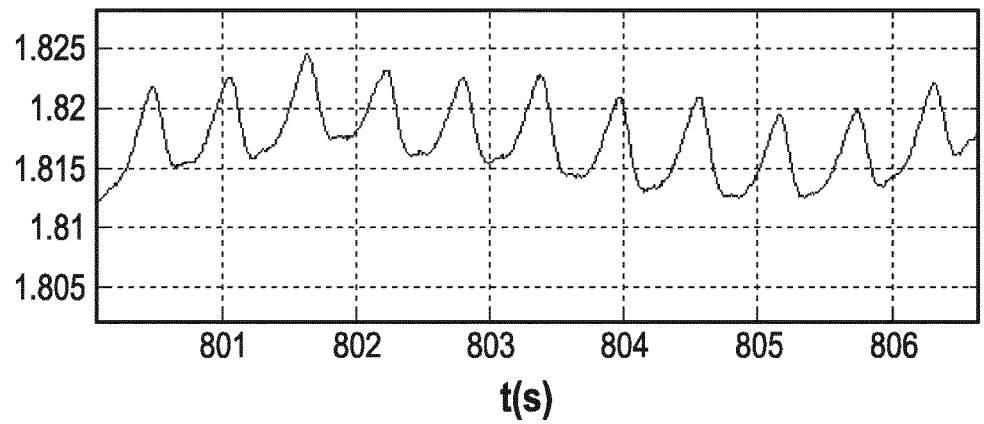
FIG. 1 shows a graph of an output signal of a PPG sensor according to the prior art.
Figure 2:
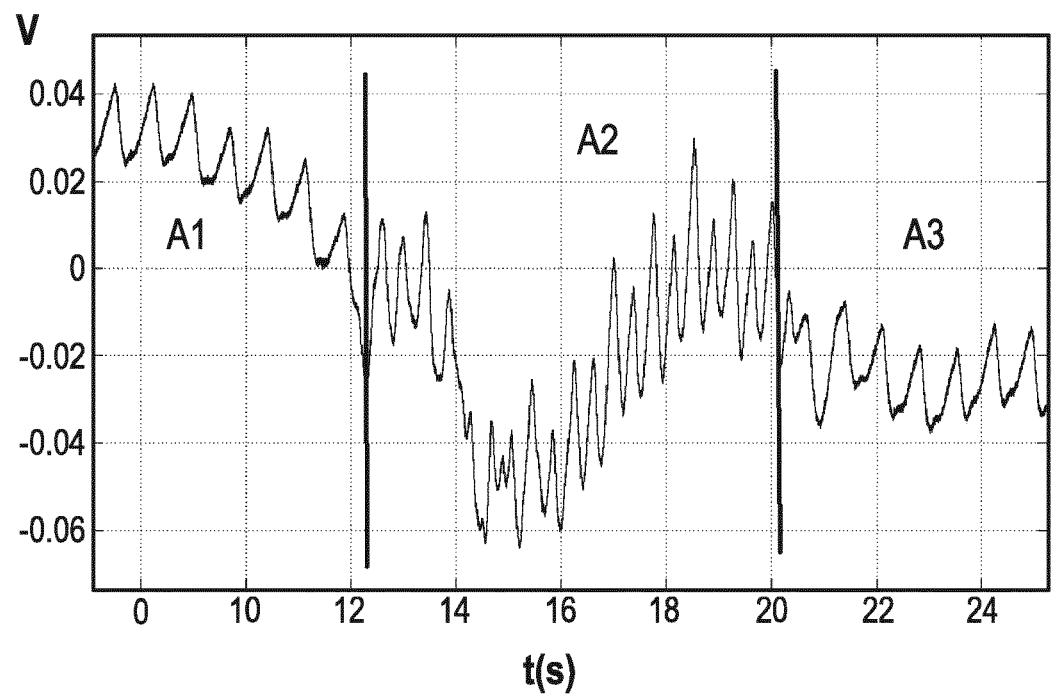
FIG. 2 shows an output signal of a PPG sensor according to the prior art.
Figure 3:
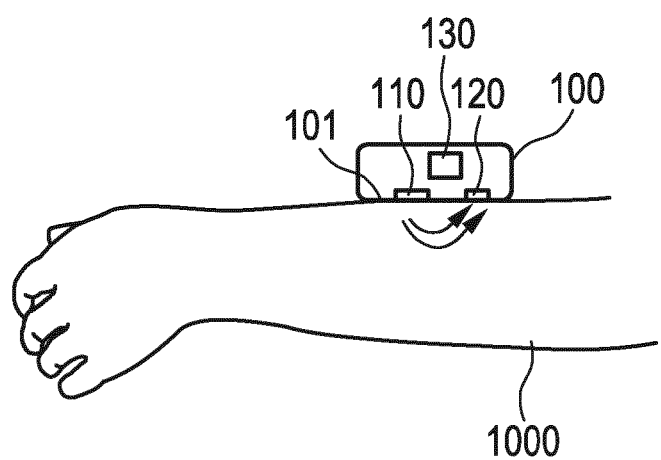
FIG. 3 shows a basic representation of an operational principle of a vital signs sensor according to an aspect of the invention.

FIG. 3 shows a basic representation of an operational principle of a vital signs sensor. In FIG. 3, a heart rate sensor 100 with its contact surface 101 is arranged or placed on for example an arm of a user. The vital signs sensor can be based on a photoplethysmograph PPG sensor. The contact surface 101 can be directly placed onto the skin 1000 of the user. The heart rate sensor 100 comprises at least one light source 110 and at least one photo detector 120. The light source 110 emits light e.g. via the contact surface 101 onto or in the skin 1000 of a user. Some of the light is reflected and the reflected light can be detected by the photo detector 120. Some light can be transmitted through tissue of the user and be detected by the photo detector 120. Based on the reflected light, vital signs of a user like a heart rate can be determined. A motion correction unit 130 is configured to correct motion artefacts from the output of the at least one photo detector 120 to improve the signal-to-noise ration and to determine a heart rate or other vital signs of the user.

The output signal of the PPG sensor gives an indication on the blood movement in vessels of a user. The quality of the output signal of the PPG sensor can depend on the blood flow rate, skin morphology and skin temperature. In addition, optical losses in the PPG sensor may also have an influence on the quality of the output signal of the PPG sensor. The optical efficiency of the PPG sensor can depend on reflection losses when light penetrates from one media into another. Furthermore, scattering of light at the surface of the skin of the user may also have an influence on the optical efficiency of the PPG sensor.

The PPG sensor or optical vital signs sensor according to an aspect of the invention can be implemented as a wrist device (like a watch or smart watch). The optical vital signs sensor can also be implemented as a device worn behind the ear of a user, e.g. like a hearing aid.

Optionally the PPG sensor according to the invention can also be implemented as non-invasive sensor, a non-contact or contact-less sensor. Such a contact-less sensor can comprise at least two (non-contact) optical fibers (one optical fiber as transmitter or light source and one optical fiber as receiver) and can be used to detect the vital signs of a user.

Figure 4:
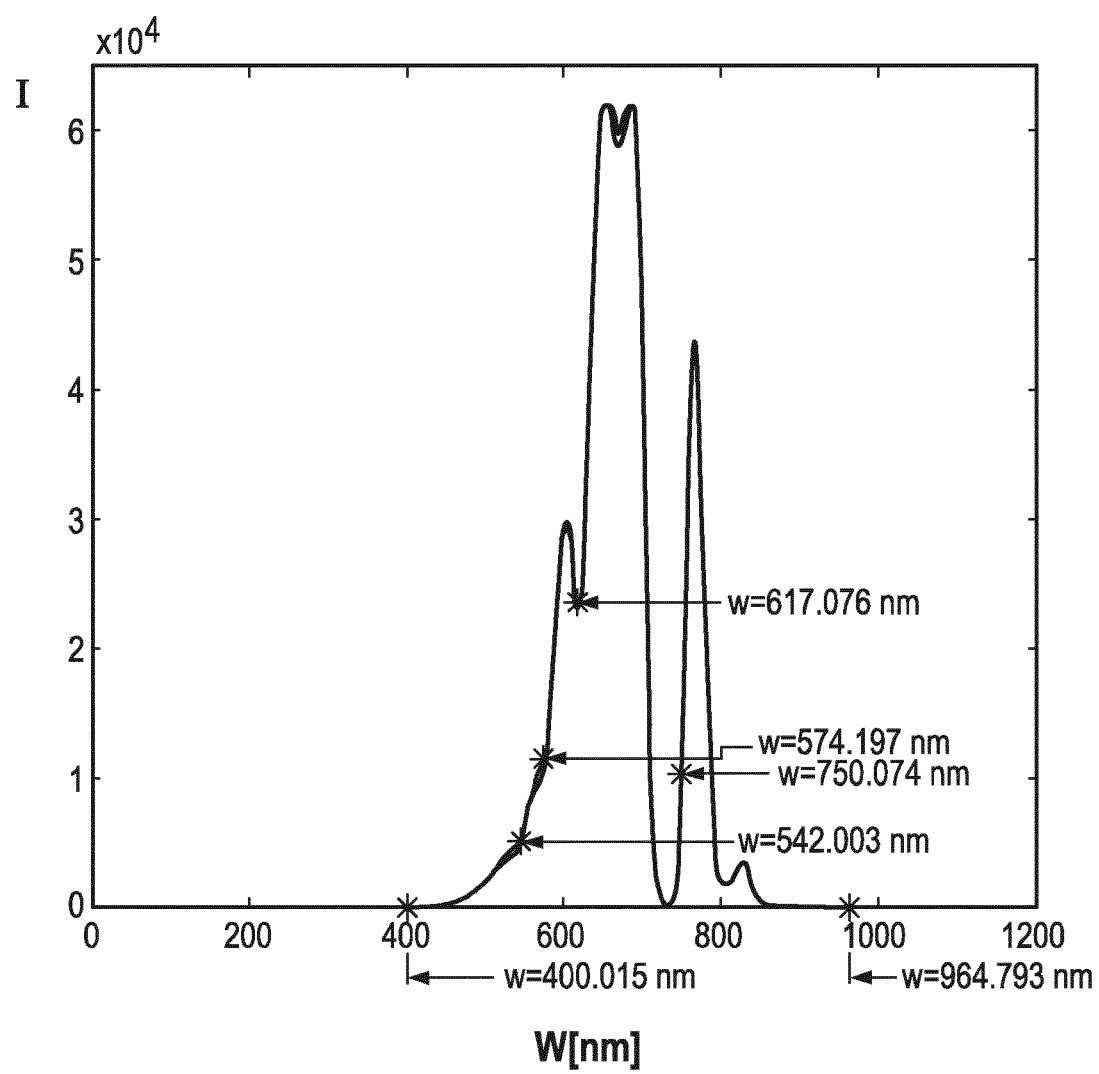
FIG. 4 shows a graph indication the intensity of light reflected from a skin of a user according to an aspect of the invention.

FIG. 4 shows a graph indicating the intensity of light reflected from a skin of a user according to an aspect of the invention. In FIG. 4, a spectrum of light I as reflected from a skin 1000 of a user is depicted over the wavelength W (nm). However, the amplitude of the reflected light can change due to the pulsation of blood as well as the movement of the user or a relative movement of the PPG sensor and the user.

Figure 5:
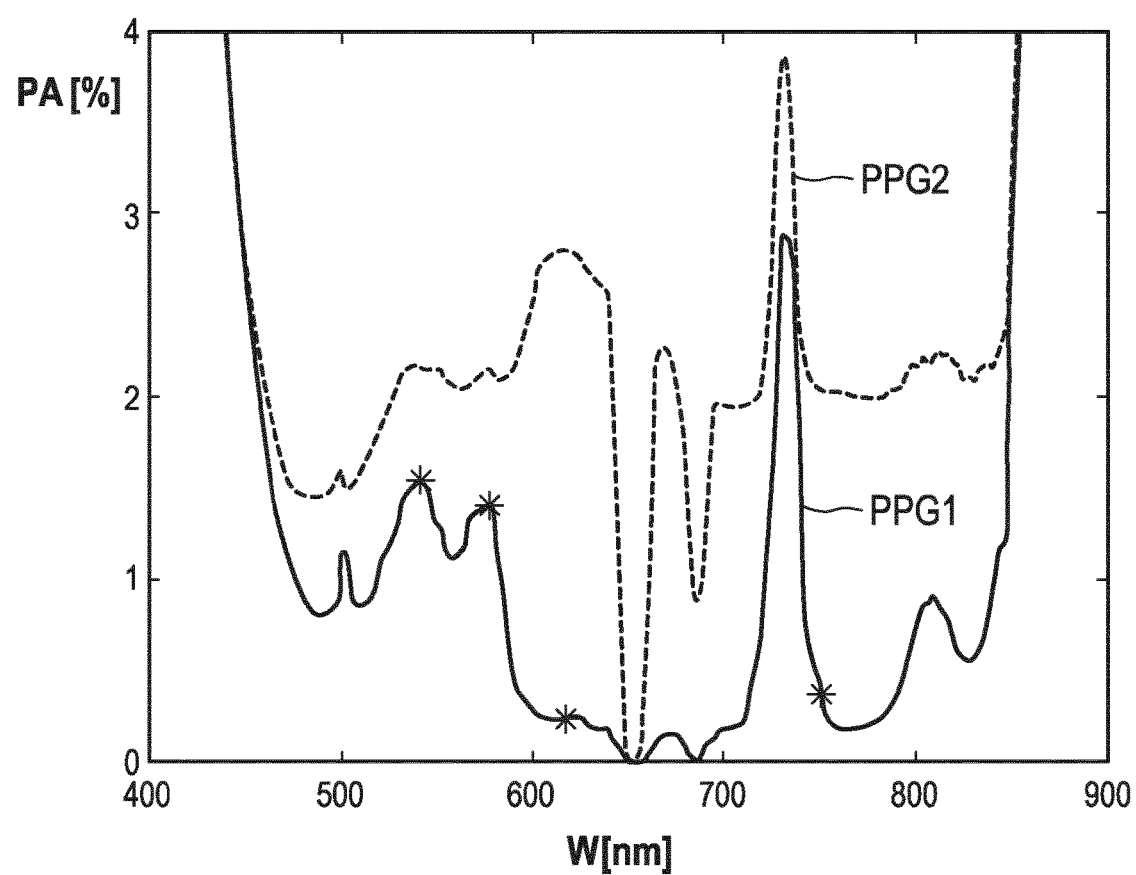
FIG. 5 shows a graph indicating the dependence of the amplitude of an output signal versus the wavelength of the light from a PPG sensor.

FIG. 5 shows a graph indicating the dependence of the amplitude PA of an output signal versus the wavelength W (nm) of the light from a PPG sensor. In FIG. 5, an amplitude of reflected light due to a motion PPG2 as well as an amplitude of reflected light due to the pulse PPG1 is depicted over the wavelength.

As can be seen from FIG. 5, the amplitude of the pulses are in particular high and distinct at wavelengths around 550 nm.

Figure 6:
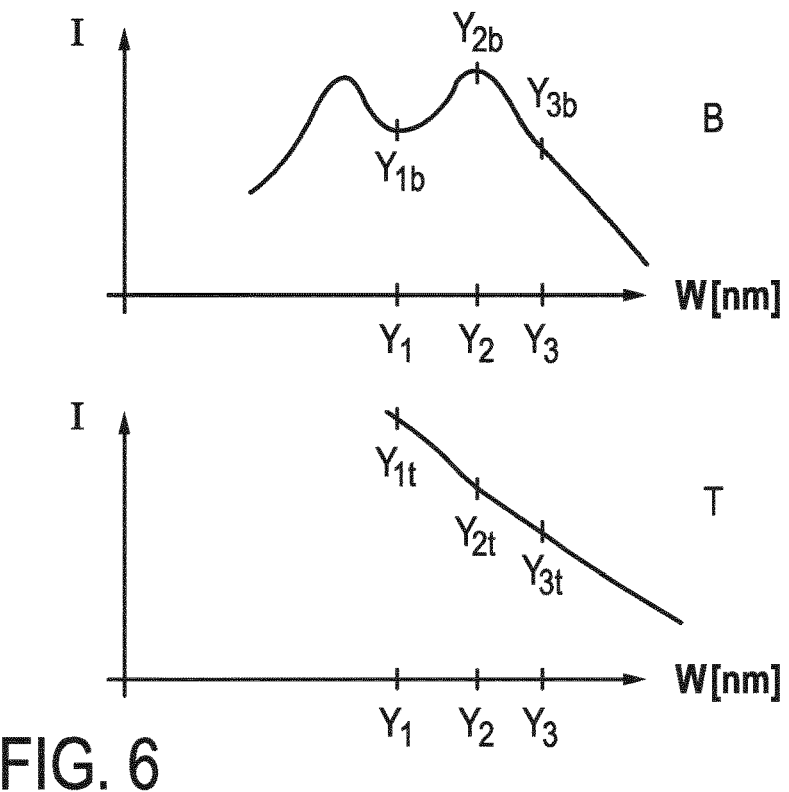
FIG. 6 shows a graph indicating a spectrum of light reflected by blood as well as a spectrum of light reflected by the tendon of the user.

FIG. 6 shows a graph indicating a spectrum of light reflected by blood as well as a spectrum of light reflected by the tendon of the user. In FIG. 6, the upper curve shows the dependence on the spectrum of light I as reflected by the blood of a user. The lower curve shows a spectrum of light I as reflected by the tendon of a user. While the light as reflected by the blood has two distinct peaks, the light as reflected by the tendon has an approximate linear decline with increasing wavelength W (nm).

Figure 7:
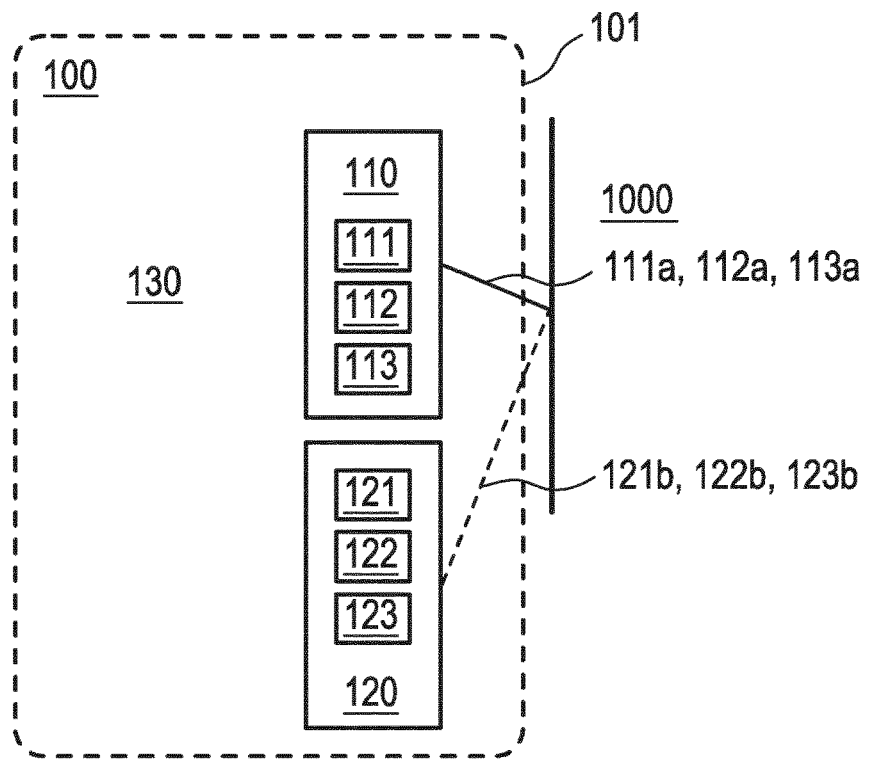
FIG. 7 shows a block diagram of an optical vital signs sensor according to an aspect of the invention.

FIG. 7 shows a block diagram of an optical vital signs sensor according to an aspect of the invention. The optical vital signs sensor 100 may comprise a contact surface 101 which can be placed in direct contact with the skin 1000 of a user. The optical vital signs sensor comprises a light unit 110 which can have three light emitting diodes 111-113. These three light emitting diodes 111-113 may emit light 111$a$, 112$a$, 113$a$ at three different wavelengths. Alternatively, the light unit 110 may also comprise one tunable light emitting diode which can emit light 111$a$, 112$a$, 113$a$ at three different wavelengths.

The optical vital signs sensor 100 furthermore comprises a photo detector unit 120 which is able to detect the reflected light 121$a$-123$c$. The light unit 110 can be able to emit light 111$a$-113$a$ at three wavelengths. The photo detector 120 may comprise three different photo diodes 121-123 which are able to detect the reflected light at the three different wavelengths 121$a$-123$b$. The output of the photo detector 120 is forwarded to the motion correction unit 130 which is performing a motion correction on the output signals. The motion correction 130 serves to remove motion artefacts from the output signal of the photo detector.

The three different wavelengths may be $Y_1$, $Y_2$ and $Y_3$. These three wavelengths $Y_1$-$Y_3$ are arranged on one of the peaks around 550 nm. According to an aspect of the invention, the output signal of the photo detector is a sum of an output signal of the photo detector due to reflected light from the blood B of the user as well as reflected light from the tendons T. The output signal $Y_b t$ can therefore be $Y_b + Y_t$, wherein the index "b" corresponds to blood and the index "t" corresponds to tendons. If this equation is applied to three points, the results thereof are as follows:

$$Y_{1bt} = Y_{1b} + Y_{1t};  \quad (1)$$

$$Y_{2bt} = Y_{2b} + Y_{2t};  \quad (2)$$

$$Y_{3bt} = Y_{3b} + Y_{3t}. \quad (3)$$

As may be deducted from FIG. 6, the coordinates of the three points may be members of an arithmetic series such that $$\frac{Y_{1t} + Y_{3t}}{2} = Y_{2t} \quad (4)$$

According to an aspect of the invention, the middle wavelength is at an equidistant position between the first and third wavelength such that $$Y_2 = \frac{Y_1 + Y_3}{2}. \quad (5)$$

According to an aspect of the invention, a motion correction can be based on the following formula:

$$Y = \frac{Y_{1bt} + Y_{3bt}}{2} - Y_{2bt}. \quad (6)$$

If the equations 1 to 4 are substituted in the above equation, it can be seen that the influence of the tendons are removed, which results in $$Y = \frac{Y_{1b} + Y_{3b}}{2} - Y_{2b}. \quad (7)$$

As $Y_{1b}$ and $Y_{3b}$ almost correspond to each other, the equation is as follows:

$$Y = Y_{1b} - Y_{2b} \quad (8)$$

Accordingly, if this formula is used, the influence of the tendons can be removed such that only the reflected light due to the blood variation is determined.

As an example, the first wavelength $Y_1$ is 530 nm, the second wavelength $Y_2$ is 550 nm and the third wavelength $Y_3$ is 570 nm. Other wavelengths are also possible as long as the second wavelength is equidistant to the first and third wavelength. In other words, the second wavelength is arranged in the middle between the first and third wavelength.

Figure 8:
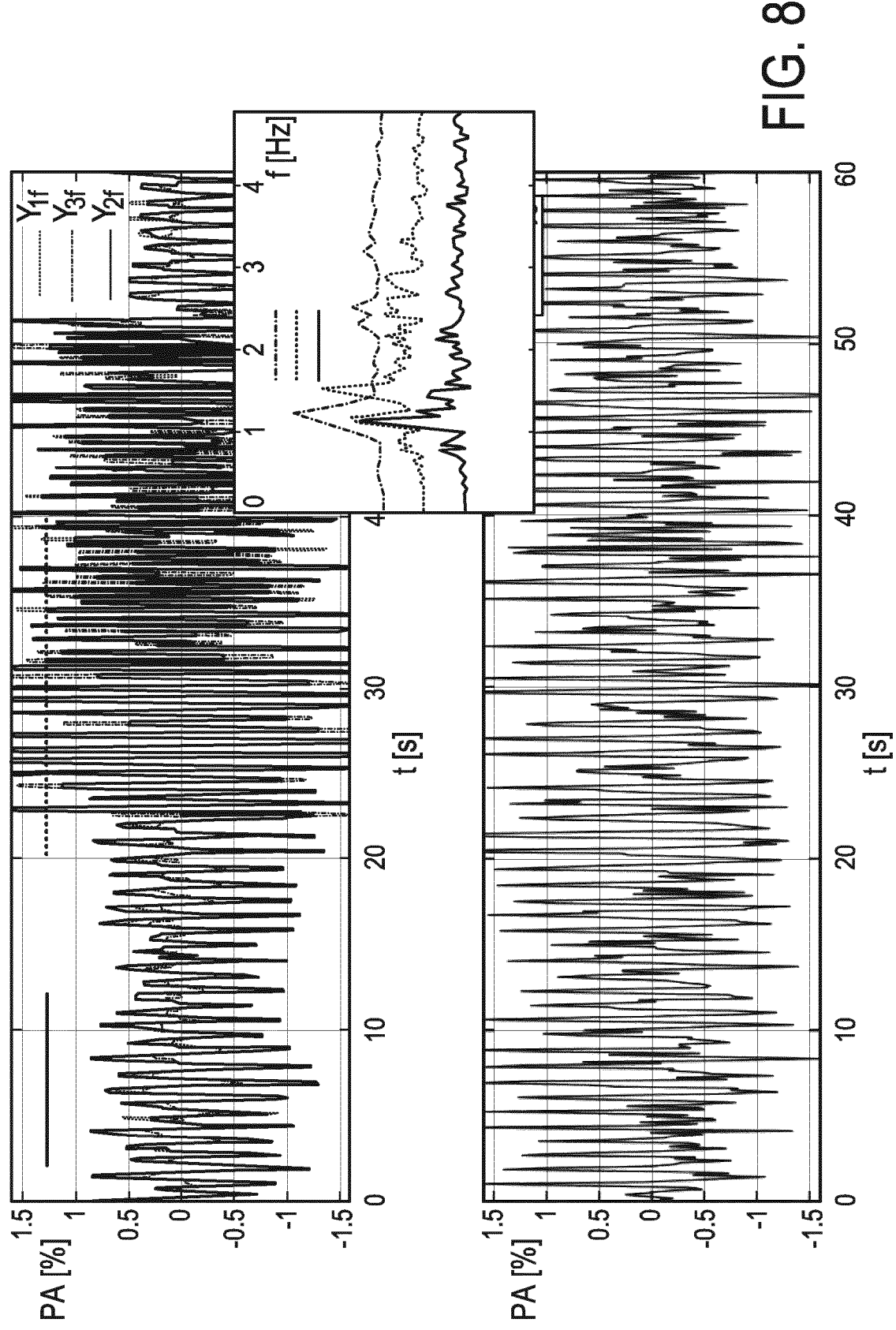
FIG. 8 shows a graph of the output signal of a PPG sensor without and with a motion correction according to an aspect of the invention.

FIG. 8 shows a graph of the output signal of a PPG sensor without and with a motion correction according to an aspect of the invention.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. An optical vital signs sensor configured to measure vital signs of a user, the optical vital signs sensor comprising:
   a light source configured to generate light at at least three wavelengths ($Y_1$-$Y_3$) which is directed towards a skin of the user, wherein the first, second and third wavelengths ($Y_1$-$Y_3$) are arranged approximately around 550 nm, wherein the second wavelength ($Y_2$) is arranged equidistantly between the first wavelength and third wavelength ($Y_1$,$Y_3$),
   a photo detector configured to detect an intensity of light at the at least three wavelengths, wherein said light is indicative of a reflection of light emitted in or from the skin of the user, and
   a computer that performs motion correction to correct motion artifacts from the light intensity detected by the photo detector, wherein performing the motion correction includes subtracting the light intensity detected at the second wavelength from an average of the light intensity detected at the first wavelength ($Y_1$) and that at the third wavelength ($Y_3$).

2. The optical vital signs sensor according to claim 1, wherein the second wavelength ($Y_2$) corresponds to approximately 550 nm, the first wavelength ($Y_1$) corresponds to approximately 530 nm, and the second wavelength ($Y_2$) corresponds to approximately 570 nm.

3. The optical vital signs sensor according to claim 1, wherein said optical vital signs sensor is a photoplethysmographic sensor.

4. The optical vital signs sensor according to claim 1, wherein the second wavelength ($Y_2$) corresponds to approximately 550 nm, the first wavelength ($Y_1$) corresponds to approximately 540 nm, and the second wavelength ($Y_2$) corresponds to approximately 560 nm.

5. The optical vital signs sensor according to claim 1, wherein the computer further determines a vital sign of the user, at least based on correcting the motion artifacts from the light intensity detected by the photo detector.

6. The optical vital signs sensor according to claim 5, wherein the vital sign of the user includes heart rate.

7. The optical vital signs sensor according to claim 1, wherein the light sources includes one or more optical fibers and the light is provided via the one or more optical fibers.

8. A method of measuring vital signs of a user with an optical vital signs sensor, the method comprising operations that include:
   generating light at at least three wavelengths ($Y_1$-$Y_3$) which are directed towards a skin of the user;
   detecting an intensity of light at the at least three wavelengths ($Y_1$-$Y_3$), wherein said light is indicative of a reflection of light emitted from the skin of the user; and
   correcting motion artifacts from the detected light by subtracting the light intensity detected at the second wavelength ($Y_2$) from an average of the light intensity detected at the first wavelength ($Y_1$), and at the third wavelength ($Y_3$),
      wherein the first, second and third wavelengths ($Y_1$-$Y_3$) are arranged approximately around 550 nm, and wherein the second wavelength ($Y_2$) is arranged equidistantly between the first and third wavelength ($Y_1$,$Y_3$).

9. The method according to claim 8, wherein the second wavelength ($Y_2$) corresponds to approximately 550 nm, the first wavelength ($Y_1$) corresponds to approximately 530 nm, and the second wavelength ($Y_2$) corresponds to approximately 570 nm.

10. The method according to claim 8, wherein the second wavelength ($Y_2$) corresponds to approximately 550 nm, the first wavelength ($Y_1$) corresponds to approximately 540 nm, and the second wavelength ($Y_2$) corresponds to approximately 560 nm.

11. The method according to claim 8, wherein said optical vital signs sensor is a photoplethysmographic sensor.

12. The method according to claim 8, further comprising:
   determining a vital sign of the user, at least based on correcting the motion artifacts from the detected light.

13. The method according to claim 12, wherein the vital sign of the user includes heart rate.

14. The method according to claim 8, wherein the light is provided via one or more optical fibers of the optical vital signs sensor.

15. A non-transitory computer readable storage medium that stores a computer program that, when executed at a computer that is controlling an optical vital signs sensor, causes performance of operations that include:
   generating, via the optical vital signs sensor, light at at least three wavelengths ($Y_1$-$Y_3$) which are directed towards a skin of the user;
   detecting, via the optical vital signs sensor, an intensity of light at the at least three wavelengths ($Y_1$-$Y_3$), wherein said light is indicative of a reflection of light emitted from the skin of the user; and
   correcting, via the computer, motion artifacts from the detected light by subtracting the light intensity detected at the second wavelength ($Y_2$) from an average of the light intensity detected at the first wavelength ($Y_1$), and at the third wavelength ($Y_3$),
      wherein the first, second and third wavelengths ($Y_1$-$Y_3$) are arranged approximately around 550 nm, and wherein the second wavelength ($Y_2$) is arranged equidistantly between the first and third wavelength ($Y_1$,$Y_3$).

16. The non-transitory computer readable storage medium according to claim 15, wherein the second wavelength ($Y_2$) corresponds to approximately 550 nm, the first wavelength ($Y_1$) corresponds to approximately 530 nm, and the second wavelength ($Y_2$) corresponds to approximately 570 nm.

17. The non-transitory computer readable storage medium according to claim 15, wherein the second wavelength ($Y_2$) corresponds to approximately 550 nm, the first wavelength ($Y_1$) corresponds to approximately 540 nm, and the second wavelength ($Y_2$) corresponds to approximately 560 nm.

18. The non-transitory computer readable storage medium according to claim 15, wherein said optical vital signs sensor is a photoplethysmographic sensor.

19. The non-transitory computer readable storage medium according to claim 15, wherein the operations further include:
   determining a vital sign of the user, at least based on correcting the motion artifacts from the detected light.

20. The non-transitory computer readable storage medium according to claim 19, wherein the vital sign of the user includes heart rate.

* * * * *